United States Patent
Basagañas Millan

(10) Patent No.: US 6,594,445 B2
(45) Date of Patent: Jul. 15, 2003

(54) HEATING DEVICE FOR THE VAPORIZATION OF ACTIVE SUBSTANCES

(75) Inventor: Jordi Basagañas Millan, Barcelona (ES)

(73) Assignee: DBK Espana, S.A., Barcelona (ES)

( * ) Notice: Subject to any disclaimer, the term of this patent is extended or adjusted under 35 U.S.C. 154(b) by 0 days.

(21) Appl. No.: 10/191,048

(22) Filed: Jun. 3, 2002

(65) Prior Publication Data
US 2002/0166853 A1 Nov. 14, 2002

Related U.S. Application Data

(63) Continuation of application No. PCT/ES00/00369, filed on Mar. 10, 2000.
(51) Int. Cl.[7] .................................................. F24F 6/08
(52) U.S. Cl. ........................................................ 392/395
(58) Field of Search ............................... 392/386, 390, 392/392, 393, 394, 395; 122/366; 239/44; 261/97, 99

(56) References Cited
FOREIGN PATENT DOCUMENTS

EP        0 451 331 A1     10/1991
EP        0 689 766 A1     1/1996
ES        1026353          4/1994

*Primary Examiner*—Sang Paik
(74) *Attorney, Agent, or Firm*—Katten Muchin Zavis Rosenman

(57) ABSTRACT

The device is based on an optionally single piece body (1), obtained by plastic molding, of cylindrical configuration, with the opening and the corresponding axial and central neck (3) for the passing of a wick that, at its lower end, is immersed in an active substance contained in a vessel to which the device is applicable, having optional ribs (4) for holding and positioning the wick heating resistances, as well as projections (6) with cross channels (7) for the positioning of the ends of the electrical resistances wires, being supplemented with a piece (8) acting as a clip, that by means of a flap or arm (9) formed in it, the ends of the resistances are kept in the flutings (7), and allows the positioning of the contactors through which the electrical supply to those heating resistances is set up, a positioning that is carried out on an upper slot (10) set up in that piece (8) which has contactor connection flaps (11), and optionally a cover that assures a more reliable fastening by pressing on the upper edge of the clips (8).

7 Claims, 4 Drawing Sheets

A-A

B-B

HEATING DEVICE FOR THE VAPORIZATION OF ACTIVE SUBSTANCES

This application is a continuation of application No. PCT/ES00/00369, filed Mar. 10, 2000.

PURPOSE OF THE INVENTION

This invention refers to a heating device for the vaporization of active substances, that is applicable to certain types of vessels containing active substances that, having a wick with one end introduced in the vessel and therefore immersed in the active substance, the opposite end of this wick emerging externally so that by capillary action the active substance reaches that external and free end, all so that the heating of the wick produce the vaporization of the corresponding active substance. The heating taking place by means of electrical resistances positioned in the device.

The purpose of the invention is to provide a heating device that includes one or more electrical resistances whose activation produces the heating of a wick that passes through an axial opening in the device, said wick being partly immersed in an active liquid substance contained in a vessel on which the actual device is mounted, the basic purpose of the invention being that the support body for the electrical resistance or resistances be formed from a single piece of moulded plastic.

BACKGROUND TO THE INVENTION

There are numerous heating devices designed to produce the vaporization of active substances, such as disinfectants, insecticides, air-fresheners, germicides, fungicides, etc., two main types being distinguishable, one of them based on the heating of a PTC element that is usually situated between two high thermal conductivity coefficient electrodes, so that, with the correct electrical supply to the electrodes, the PTC referred to is heated and the consequent vaporization of an active substance that, by capillary action, reaches the free and upper end of a wick that emerges through an axial opening provided in the device assembly, this being mounted in the entrance of the vessel, containing the active substance.

As an example of this first type of device, the Patent of Invention 9600482 might be quoted, where the device is made up with a minimum number of pieces that logically facilitate its assembly and reduces manufacturing costs, among other advantages.

A second type of device is based on the heating of the wick by means of electrical resistances, and in this sense Spanish Utility Model N° 9501364 and the European Patent EP 0689766 A1 can be quoted, so that in the first case the heating device includes a multitude of pieces that must be suitably assembled for the operation to be effective, which undoubtedly requires qualified personnel, care in assembly, etc., while in the second case, in the device of the European Patent, the electrical resistances are mounted on a printed circuit with an adequate power supply which requires an appropriate space or area within the device assembly for the positioning and correct placing of the printed circuit board.

Evidently, the use of electrical resistances is more economic than the use of PTC elements, although, as has just been stated, the two types of devices referred to, and that include electrical resistances as heating elements, have drawbacks not resolved at present.

DESCRIPTION OF THE INVENTION

The heating device that is proposed has been planned precisely to resolve the forementioned difficulties, for which a body has been envisaged in which the electrical resistances or resistance are mounted, in the case of there being only one, and with a supplementary piece acting as a clip set up on the actual body the effective and proper connection of the ends of the electrical resistances with the corresponding contactors is achieved, all in a such way that the said body for all the unit is formed from a single piece of moulded plastic, the preferred material being polyoliphene, such as polyamide, of low cost and, since it allows the possibility of working at a higher temperature, is more appropriate.

More specifically, the plastic moulded body as a single part of the device, supplemented by the forementioned clip, has a cylindrical configuration with a concentric opening fitted with an axial neck, so that between this neck and the side surface of the cylindrical body a diametrically opposed pair of ribs are established, for locating each resistance, with the particularity that in the case that three heating resistances were mounted in the device, then the number of ribs would be three, arranged about a 180° contour, with which the angular separation would be 90°, as two of them remain diametrically opposite each other.

In this way the resistance or resistances are secured, these can be MO(metal oxide), ceramic, coiled wire, carbon or silicon type.

The body, besides the previously mentioned ribs, also has internal projections, whose number will be similar to the number of resistances plus one in the case of mounting in series, and equal to the number of resistances in the case of mounting in parallel, which projections are fitted with a pair of flutes forming a cross for the positioning of the ends of the wires of the electrical resistances, and the corresponding connection of the adjacent ends of two resistances, with the particularity that in those cross channels of the forementioned projections the ends of the resistances connected to each other can remain perfectly secured, and these staying supported by themselves without the need of the forementioned ribs.

As regards the part or piece that acts as a clip to establish electrical contact between the corresponding contactors and the ends of the heating resistance wires, it consists of a rectangular metallic sheet part, with an arm obtained by making a cutaway without detaching material, setting up a horizontal support surface on the upper part of the projections in which the ends of the heating resistance wires are positioned, preventing these wires from leaving the channels formed in those projections, and at the same time allowing the connection with the contactors, that are duly guided through a slot formed lengthwise in the upper and vertical section of the corresponding clip, in which there are some flaps, also obtained by making a cutaway without detaching the material, for establishment the corresponding connection.

Optionally the assembly or device in question can incorporate a cover with complete closing of the unit, in order to provide it with greater safety and not to leave the resistances nor their wires exposed, neither of course the contactor attachment clips, although the absence of the cover doesn't imply that the device doesn't offer maximum safety, since the assembly is placed within a general casing.

The cover, when it is included in the unit, will be fitted to the base of the heater and to its chimney, being supported only by the upper edge of the walls and respecting the irregular shape of that wall, without adding any height to the device when seen without the cover. Furthermore, such a cover will give a greater reliability in the positioning of the clips, being supported by them by means of three or four supports depending on whether two or three resistances are used in the heater.

By means of the device referred to a cost reduction is achieved due to the fact that resistances are more economic components than the PTC elements, the cost being similarly reduced due to the simplification of the number of parts and to the elimination of the corresponding closing cover, without forgetting that energy use is optimum compared with other devices with the same purpose.

DESCRIPTION OF THE DRAWINGS

To supplement this description and with the aim of leading to a better understanding of the characteristics of the invention, in accordance with a preferred example of its practical embodiment, as an integral part of this description it is accompanied by a set of drawings where in an illustrative and non-limiting way, the following have been represented.

PREFERABLE EMBODIMENT OF THE INVENTION

Figure 1:
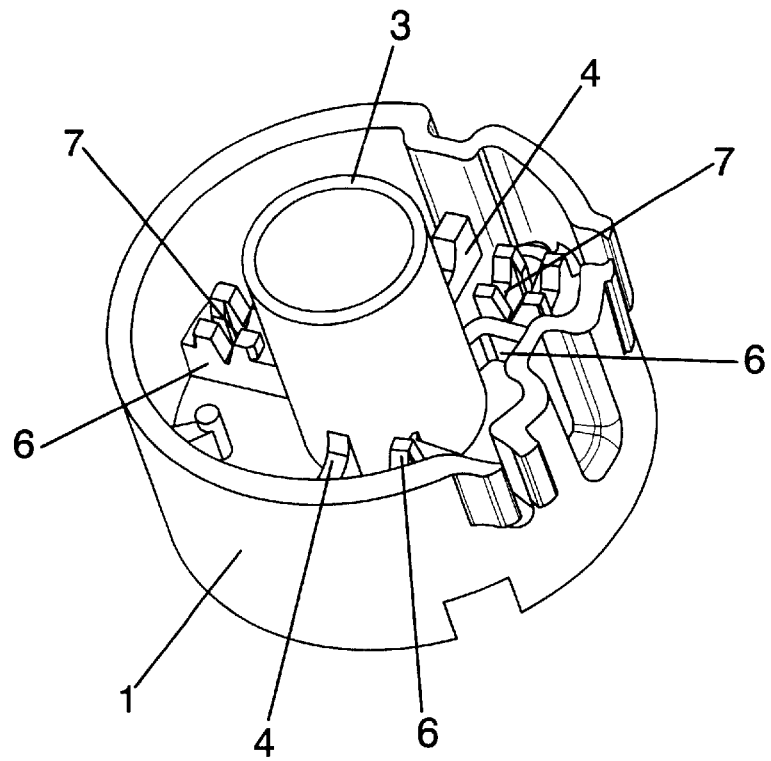
FIG. 1. Shows a representation of a general perspective of the single piece plastic moulded body of the invention device.
Figure 2:
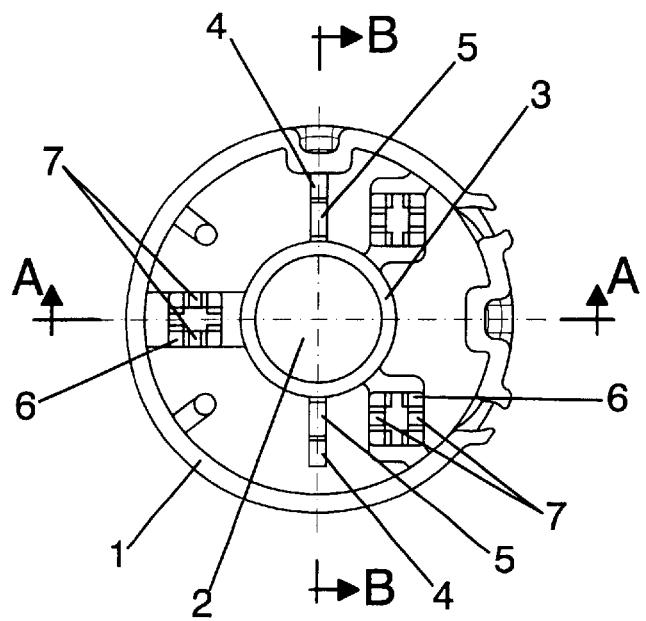
FIG. 2. Shows a plan view of the body shown in the previous figure.
Figure 3:
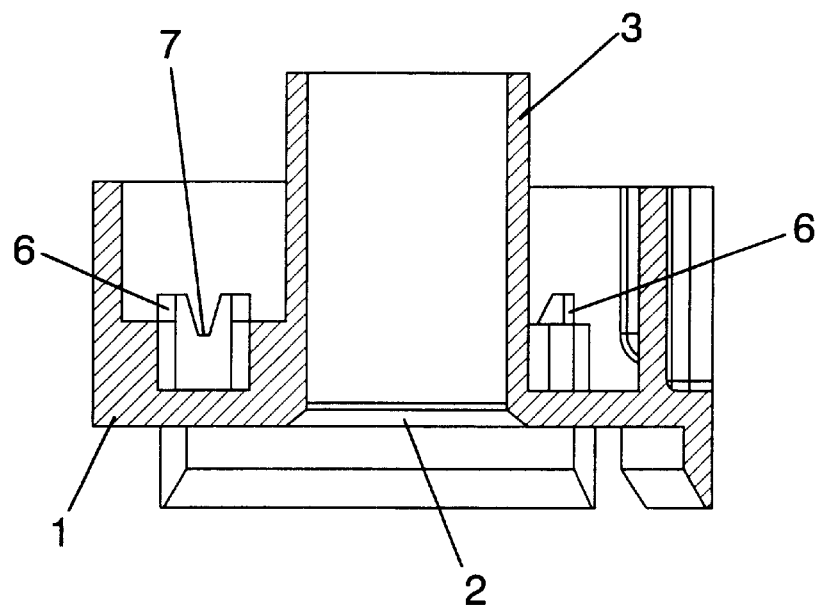
FIG. 3. Shows a view corresponding to the section A—A of the previous figure.
Figure 4:
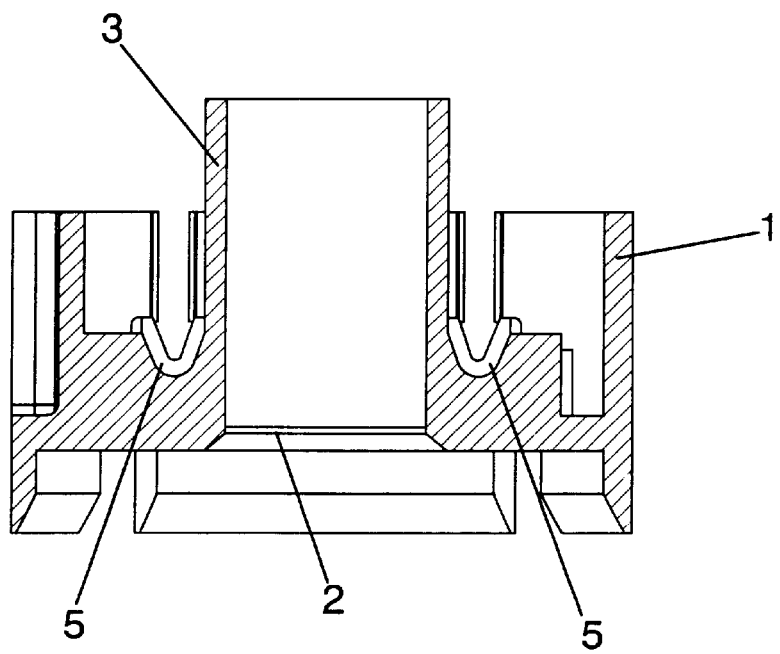
FIG. 4. Shows another section view, in this case corresponding to the sectioning line B—B of FIG. 2.

As can be seen in the figures referred to, the heating device for the vaporization of active substances, that is the subject of the invention, is make up starting from a cylindrical general body (1) derived from a single piece of moulded plastic, preferably of polyoliphene, such as polyamide, a cylindrical body (1) that has a concentric opening (2) with an axial neck (3) for passing a wick that, as has already been said throughout the present description, is housed inside the interior of a vessel containing an active substance that it is intended to vaporize, the wick emerging upwards through the neck (3) so that the active substance reaches this free end by capillary action, it being necessary to heat the wick to produce the vaporization of the continuously replaced active substance.

In any case, the body (1) as the basic part of the heating device, has ribs (4) set up between the side surface of the neck (3) and the internal side surface of the cylindrical surface of the body (1), ribs (4) that have fluting (5) for positioning the corresponding electrical resistances, so that in each rib (4) and specifically in their fluting (5) a resistance will be placed, so that that in the case that the device incorporates two electrical resistances, the number of ribs (4) will be two, placed diametrically opposite, while if three resistances are incorporated the number of ribs (4) would be three.

Figure 5:
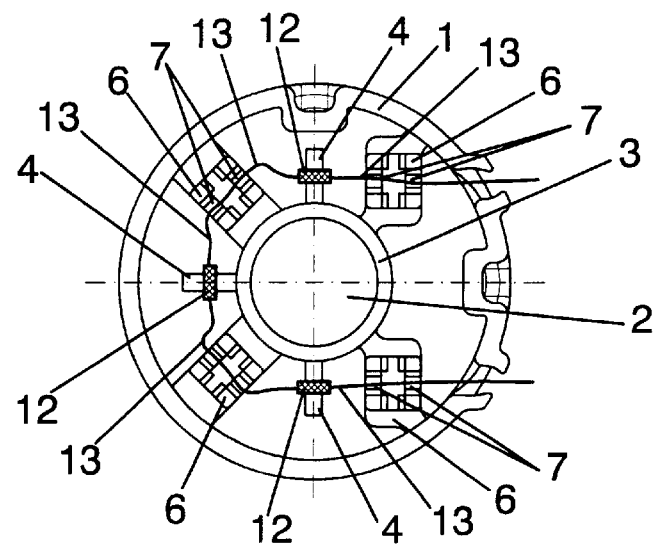
FIG. 5. Shows a plan view of the body in a variation of the embodiment to have three resistances, which appear mounted on their respective ribs.

In FIG. 5, specifically, is shown the variant embodiment of the body (1) with three ribs (4) for supporting this many resistances (12), two of these three ribs are placed diametrically opposite each other, and the third angled at 90° with respect to them, that is, in an intermediate position.

Besides those ribs (4) the body (1) has projections with cross channels (7) set up on the upper side for positioning and immobilizing the corresponding ends of the wires (13) of the electrical resistances (12) that are positioned in the ribs (4), so that the number of those projections (6) will finally depend on the type of electrical setup selected for the resistances:

1) in the case of a series setup, it will be equal to the number of resistances plus one. Logically each projection (6) and therefore their flutes (7) will position the joined ends of two adjacent resistances, two projections having to be left for setting up the ends of the two resistances to which the corresponding connectors for an electrical supply are connected, since the connection between the resistances is in series. Therefore the number of resistances (12) that the heating device has to have can be two, in which case the number of the projections (6) will be three; and if the number of resistances (12) is three, the number of projections (5) will be four, and so forth, while the number of ribs (4) has to be the same one as that of resistances.

2) in the case of a parallel setup, it will be equal to the number of resistances.

Consequently, and as previously there has been said, the resistances (12) are placed and are supported in the fluting (5) made in each of the ribs (4), while the ends of the wires (12) of those resistances will remain positioned in the channels (7) of the projections (6)

Figure 6:
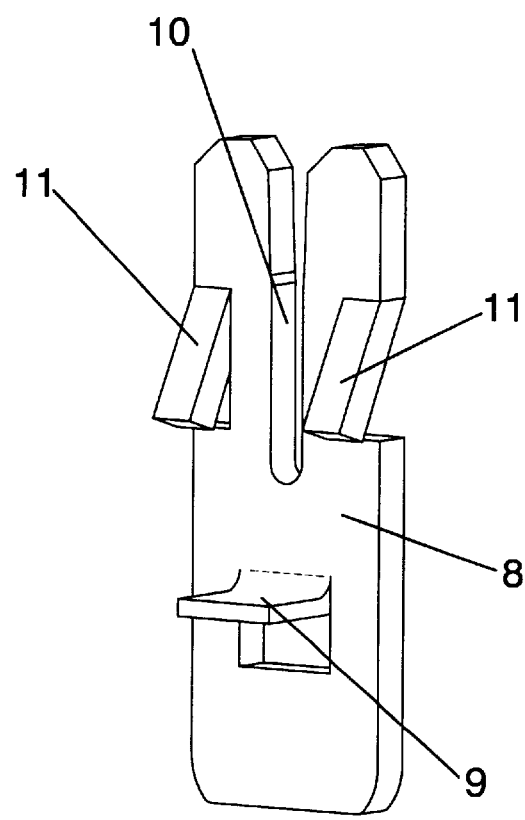
FIG. 6. Shows a general perspective representation of the clip by means of which the connection between the heating resistances that must be positioned on the body, as shown in the previous figures, and the respective electrical supply contactors, is established. This metallic and laminate clip or piece forming an independent component, although associated with the body of the device.
Figure 7:
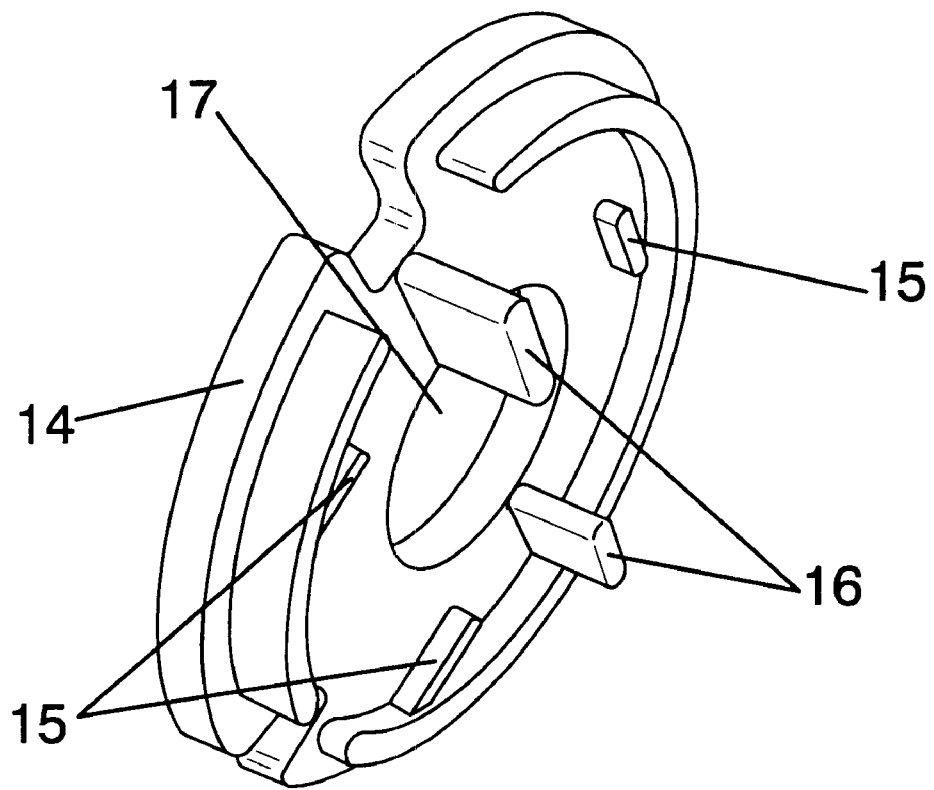
FIG. 7. Shows, finally, a perspective representation of the optional cover that the device can incorporate.

The connection of the ends of the resistances (12) that is, of the wires (13) of these last two, to the corresponding electrical supply connectors, it is made with the assistance of a clip (8) shown in FIG. 6, which is a metallic rectangular piece with some cutaways without detachment of the material, that create a flap or arm (9) perpendicular to the body or plane of the actual piece (8), so that this flap or arm (9) will be positioned leaning on the upper part of the projections (6) pressing the ends of the resistance wires onto the channels (7), holding them in their position, at the same time that the piece (8) has an upper slot (10) in which the contactors that will remain connected through the shaped flaps (11), are positioned, also by cutaways in the sides of that piece (8).

The clip that makes up that piece (8) assures the clipping of the wires (13) of the electrical resistances (12) in the flutings (7) made in the projections (6), because the flap or arm (9) leans on the upper end of the projections (6) preventing the mentioned ends of the wires from accidentally leaving the channels (7) made in those projections (6).

Furthermore, that piece or clip (8) allows the insertion of the contactors, on being positioned in the slot (10) set up in the upper part of this piece (8) contacting with the resistances, in the case that the number of these is greater than one.

On the other hand, the optional cover (14) when it is used, is mounted on the body of the heater supported with small ribs (15), equal in number to the number of clips used, on the upper edge of these clips (8), this layout forming a cross. Also it has a pair of ribs (16) of notable size, acting as positioners and planned to restrict the movements of the resistances (12) without touching them, obviously, this cover (14) has an opening (17) for positioning the neck (3) of the body (1)

It must also be said that the piece (8) allows the mounting of the actual resistances, because the assembly machine, using clamps, will hold the clip or piece (8) by the arm (9), putting the necessary pressure on this to screen its insertion or clipping.

What is claimed is:

1. Heating device for the vaporization of active substances, such as insecticide, air-freshener, perfume, etc. in which a wick that is immersed in an active substance is heated to produce the vaporization of the active substance, the heating device comprising:

a plastic body molded as a single part having a central opening and an axial neck adapted for passage of a wick to be heated, said plastic body being of cylindrical configuration and having a series of internal ribs with flutings for positioning, by direct holding, of heating resistances, said heating resistances having wires interconnecting said resistances, said wires having an ends, said plastic body further comprising projections having upper cross channels for the positioning of the ends of the wires of the hearing resistances, and clips for holding the ends of the wires of the resistances (12) in the upper cross channels of the projections, and for maintaining electrical contact with the ends of the wires and with power supply connectors connected to said heating device.

2. Heating device for the vaporization of active substances, according to claim 1, wherein the internal ribs are positioned relative to the projections so that the heating resistances are able to remain suspended in the air by means of clipping the wires and the positioning of the wires in the flutings of the projections.

3. Heating device for the vaporization of active substances, according to claim 1, wherein the number of projections is equal to the number of heating resistances plus one in the case of a series setup, while in a parallel setup the number of projections is equal to that of the number of heating resistances.

4. Hearing device for the vaporization of active substances, according to claim 1, further comprising two diametrically opposite internal ribs for mounting two heating resistances and three projections.

5. Heating device for the vaporization of active substances, according to claim 1, further comprising three internal ribs for the mounting of three hearing resistances, two of said internal ribs being placed diametrically opposite each other, so that the third internal rib is placed in an intermediate and at an equal angle position with respect to the other two internal ribs, and four projections.

6. Heating device for the vaporization of active substances, according to claim 1, wherein each clip is metallic rectangular and has a flap for leaning on the projections and for passing against the ends of the wires of the heating resistances to prevent the wires from leaving the upper cross channels the clip having an upper slot adapted for positioning the power supply connectors and flaps adapted to secure the power supply connectors provided in the heating device.

7. Heating device for the vaporization of active substances, according to claim 1, further comprising a cover fitted with a pair of positioners for engagement with the heating resistances and other ribs that are smaller than the positioners and that press on the clips.

* * * * *

UNITED STATES PATENT AND TRADEMARK OFFICE
CERTIFICATE OF CORRECTION

PATENT NO. : 6,594,445 B2
DATED : July 15, 2003
INVENTOR(S) : J. B. Millan

It is certified that error appears in the above-identified patent and that said Letters Patent is hereby corrected as shown below:

Title page,
Item [63], please delete the existing Related U.S. Application Data and insert therefore, -- Continuation of application no. PCT/ES00/00369, filed on October 3, 2000. --

Column 1,
Delete lines 4-5 and insert therefore, -- This Application is a continuation of application no. PCT/ES00/00369, filed on October 3, 2000. --

Signed and Sealed this

Fourth Day of November, 2003

JAMES E. ROGAN
*Director of the United States Patent and Trademark Office*